(12) United States Patent
Williams et al.

(10) Patent No.: US 10,335,312 B2
(45) Date of Patent: Jul. 2, 2019

(54) VAGINAL RING REMOVAL DEVICE AND METHODS

(71) Applicants: Lutrell Trumane Williams, Greensboro, NC (US); Malika Manley Williams, Greensboro, NC (US)

(72) Inventors: Lutrell Trumane Williams, Greensboro, NC (US); Malika Manley Williams, Greensboro, NC (US)

( * ) Notice: Subject to any disclaimer, the term of this patent is extended or adjusted under 35 U.S.C. 154(b) by 215 days.

(21) Appl. No.: 15/731,767

(22) Filed: Jul. 31, 2017

(65) Prior Publication Data
US 2019/0029874 A1    Jan. 31, 2019

(51) Int. Cl.
| | |
|---|---|
| *A61F 6/12* | (2006.01) |
| *A61K 9/00* | (2006.01) |
| *A61F 6/18* | (2006.01) |
| *A61K 9/02* | (2006.01) |
| *A61F 6/14* | (2006.01) |

(52) U.S. Cl.
CPC .................. *A61F 6/12* (2013.01); *A61F 6/18* (2013.01); *A61K 9/0039* (2013.01); *A61F 6/142* (2013.01); *A61K 9/02* (2013.01)

(58) Field of Classification Search
CPC .............. A61F 6/12; A61F 6/18; A61M 31/00
See application file for complete search history.

(56) References Cited

U.S. PATENT DOCUMENTS

| | | | | |
|---|---|---|---|---|
| 622,386 | A * | 4/1899 | Perry | A61B 17/320708 606/160 |
| 1,260,187 | A * | 3/1918 | Gourley | D05B 91/04 223/101 |
| 1,355,298 | A * | 10/1920 | Bauman | D05B 91/04 87/52 |
| 2,192,795 | A * | 3/1940 | Meek | A45D 6/04 132/266 |
| 3,749,099 | A * | 7/1973 | Cotey | A61B 17/4208 30/298 |
| 4,720,026 | A * | 1/1988 | Feuerman | D05B 85/00 223/101 |
| 4,852,586 | A * | 8/1989 | Haines | A61F 6/04 128/842 |
| 5,036,589 | A * | 8/1991 | Heinrich | B26B 27/007 132/73 |
| 10,052,225 | B2 * | 8/2018 | O'Mara | A61F 6/18 |
| 2007/0102003 | A1 * | 5/2007 | Newman | A61F 6/12 128/837 |

* cited by examiner

*Primary Examiner* — Kristen Matter

(57) ABSTRACT

Devices and methods for removing an intravaginal drug delivery ring are shown and described. In one embodiment, the device is an integral one-piece moisture impermeable structure that includes a closed end finger cot and a substantially rigid hook. Typically, the closed end finger cot includes a finger opening, a compression band, and an expandable sleeve. In some examples, the distal end of the hook is aligned substantially parallel to an axis of the finger cot to properly position the user's finger with the intravaginal drug delivery ring in the vaginal canal. The result is devices and methods to improve removal of intravaginal drug delivery rings and similar contraception prevention units.

19 Claims, 5 Drawing Sheets

VAGINAL RING REMOVAL DEVICE AND METHODS

FIELD OF THE TECHNOLOGY

The present disclosure relates generally to contraceptive protection unit removal, and more particularly to an improved device, system, and methods of intravaginal drug delivery ring removal.

BACKGROUND

Millions of women now use vaginal rings as drug delivery devices designed to provide controlled release of drugs for intravaginal administration over extended periods of time. The ring is manually inserted into the vagina, typically at home or the like, and provides contraception protection. Leaving the ring in for three weeks slowly releases hormones into the body, such as estrogens and/or progestogens into the body. These hormones typically stop ovulation and thicken the cervical mucus, creating a barrier preventing sperm from fertilizing an egg. Typically, the vaginal ring is worn continuously for three weeks followed by a week off, thus each vaginal ring provides about one month of birth control.

One problem associated with the vaginal rings is the often-challenging removal process. While some women have little or no problem using a finger to loop the ring and pull the ring out of the vagina, many other women find the task demanding and unreasonably uncomfortable. For instance, women come in all shapes and sizes, and so do their respective fingers and vaginal cavities. Due to these physical differences and limitations, many women find it difficult to properly reach and retrieve the vaginal ring, particularly when the ring, or the like, is positioned against the cervix. There is a myriad of techniques proffered by the medical community to aid in the removal of the rings; however, they fail to overcome many of the difficulties and discomfort faced by women during the removal process.

A further problem associated with conventional removal processes is hygienic and health concerns. For instance, when a woman is having difficulty removing the ring, she can usually feel the ring with her fingertip, but is unable to sufficiently engage the ring with enough of her finger in order to remove it. Many women thus scratch or otherwise irritate the vaginal cavity during the at-home procedure. Further, in some situations the ring is difficult to locate and/or is too slippery to grab with fingertips alone due to natural secretions within the vaginal cavity.

Therefore, Applicants desire devices, systems, and methods for properly reaching and engaging a vaginal ring, or the like, without the drawbacks presented by the traditional systems and methods.

SUMMARY

In accordance with the present disclosure, devices are provided for removing contraception units. This disclosure provides improved devices, systems, and methods that are convenient, comfortable, and safe for the user, particularly when used to remove intravaginal contraception protection units.

One aspect of the present disclosure is to provide a device for removing an intravaginal drug delivery ring. The device includes an integral one-piece closed end finger cot and a substantially rigid hook. Typically, the closed end finger cot includes a finger opening, a compression band and an expandable sleeve that is adapted to enclose a user's finger. Further, the hook includes an elongated body that extends substantially one hundred and eighty degrees, or similar bend, from the finger cot. The distal end of the hook typically includes an enlarged knob that is generally aligned substantially parallel to an axis of the finger cot. Further, the enlarged knob is aligned at an angle offset from the finger opening axis. In addition, the enlarged knob includes a diameter that is generally greater than the elongated body. The enlarged knob is typically spaced about eight millimeters from the elongated body, and is thereby generally adapted to engage a folded intravaginal drug delivery ring.

Another aspect of the disclosure is to provide a device for removing an intravaginal contraceptive protection unit. The device includes an expandable finger cot and a substantially rigid hook that is adjacent to the finger cot. The expandable finger cot is adapted to enclose at least one finger. The substantially rigid hook is generally adjacent to the finger cot and includes an elongated body and an engagement knob. Typically, the engagement knob is positioned below at least a portion of the elongated body and is thereby substantially parallel to an axis of the finger cot.

In some examples, the intravaginal contraceptive unit is chosen from a drug delivery unit, a male condom, a female condom, a combination thereof, and the like. The hook may generally extend away from the finger cot in a first direction and towards the finger cot in a second direction. The finger cot may include a finger opening and a compression band. The engagement knob may be offset from the finger cot. The engagement knob may be offset at an angle in the range of about seven degrees to about forty degrees from the finger cot.

In other examples, the distance between the engagement knob and the elongated body is about is about twice the height of the hook's elongated body. The closed end of the finger cot may be substantially parallel with the finger opening. The hook's elongated body may include about a one hundred and eighty degree curve. Further, the knob may be adapted to engage a folded intravaginal drug delivery ring.

Another aspect of the disclosure is to provide a device for removing an intravaginal drug delivery ring, wherein the device includes an integral one-piece closed end finger cot and substantially rigid hook. The closed end finger cot typically includes a finger opening, a compression band, and an expandable sleeve. The hook typically extends away from the finger cot in a first direction and towards the finger cot in a second direction. Further, a distal end of the hook is typically aligned substantially parallel to an axis of the finger cot and at an angle offset from the finger opening axis.

In particular examples, the finger cot is a flexible sleeve with a moisture impermeable layer chosen from any variety of synthetic and/or natural materials, including for example, latex, polyurethane, polyisoprene, lambskin cellulose, a combination thereof, and the like. The finger cot may be an elongated sleeve that is generally adapted to enclose a finger. The distal portion of the finger cot may include an upper tapered wall. The closed end of the finger cot may be substantially parallel with the finger opening.

In yet further examples, the hook includes a wide proximate base adjacent the closed end of the finger cot. The hook may include an elongated substantially one hundred and eighty degree curved body. The distal end of the hook includes an enlarged knob that is generally adapted to engage the ring. The hook may extend away from the finger cot and is thus is generally adapted to engage an intravaginal drug delivery ring, for instance a folded intravaginal drug delivery ring.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
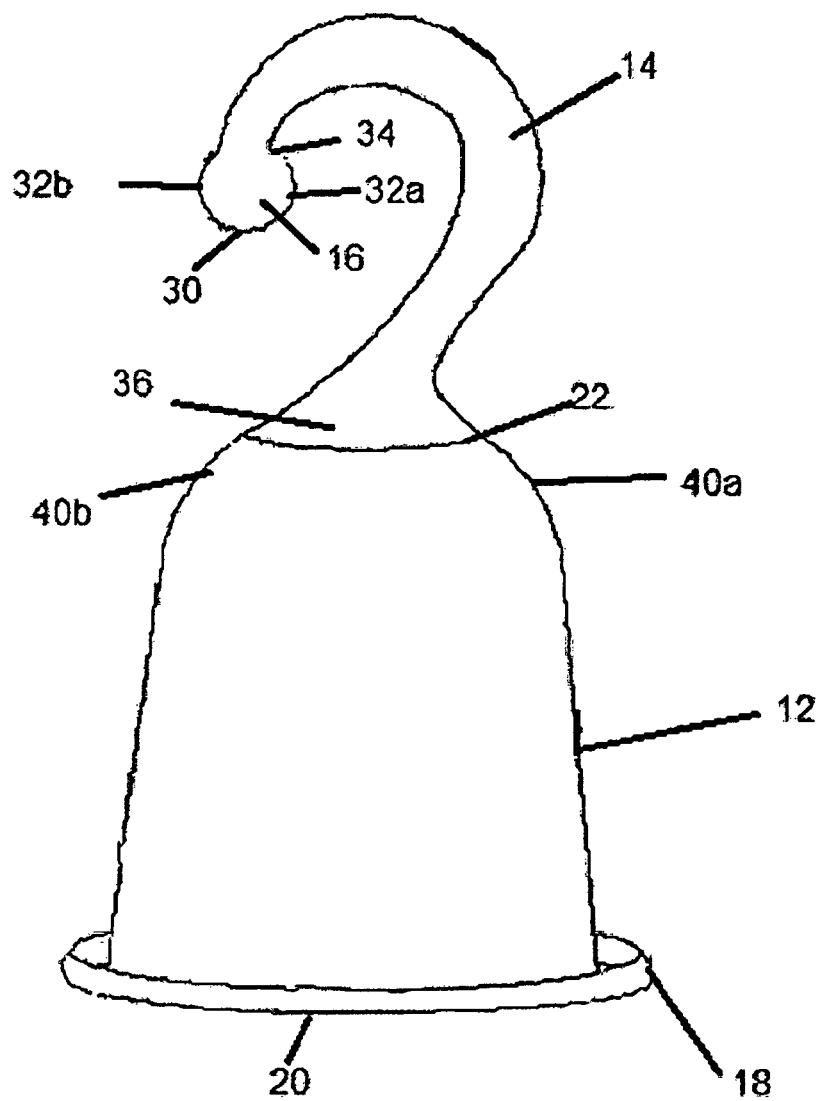
FIG. 1 is a front perspective view of a removal device according to an embodiment of the disclosure.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing embodiments of the disclosure and are not intended to limit the disclosure or any invention thereto. As best seen in FIG. 1, a removal device 10 is shown embodied according to the present disclosure. The removal device 10 is an integral unit of a finger cot 12 and hook 14 that is generally adapted to remove a birth control ring, lost condom, or the like, from the vaginal cavity, and against the cervix in particular.

As shown in FIG. 1, the removal device 10 may be an at-home apparatus that is configured to engage a user's finger and then be inserted into the vaginal cavity to remove a drug delivery ring or other conception prevention unit. The removal device is typically a single use, disposable unit. The lower portion of the removal device 10, i.e. the finger cot 12, includes a finger entry 20, a compression band 18, and an upper wall that is aligned with the hook 14. Examples of the finger cot 12 include a variety of width and length dimensions, however the finger cot is generally an expandable sleeve that is adapted to secure and enclose a user's finger. The finger cot 12 is generally a moisture impermeable layer and may be constructed out of any variety of elastic material, including latex, polyurethane, polyisoprene, lambskin cellulose, a combination thereof, and the like. In many examples, the lower portion of the finger cot 12 includes a compression band 18, or similar layered material, to generally form a substantially tight seal around the finger to ensure the integral unit is not lost in the vaginal cavity during use.

FIG. 1 illustrates one example of the finger cot wherein the upper portion is tapered 40*a*, 40*b* toward a closed end 22. The closed end 22 abuts the hook 14 assembly. Those of ordinary skill in the art having the benefit of this disclosure will recognize that a variety of tapered portions 40*a*, 40*b* and closed ends 22 may be provided to enclose the wearer's finger as shown and described herein.

As shown in FIG. 1, the hook 14 is typically a substantially rigid, yet soft, member to withstand minor bending and/or rotation during operation but gentle on the user. The hook 14 generally includes an elongated body that extends from the closed end 22 of the finger cot 12 to the enlarged engagement knob 16 on its distal end. In some examples, the elongated body includes a tapered portion 36 protruding from the closed end 22 to generally define a streamlined connection between the finger cot 12 and the hook 14 that is free of protrusions and disturbances. The enlarged knob 16 is generally adapted to engage any of the rings or other contraception prevention units. As illustrated in FIG. 1, the enlarged knob 16 may include opposing faces 32*a*, 32*b* to contact and then engage the ring, respectively. The distal end of the enlarged body may include a diameter that is sufficiently smaller than the enlarged knob to provide a nook 34 for proper leverage helpful to remove any of the rings and units shown and described herein. In one example, the diameter of the distal end of the enlarged body is about two to about ten millimeters, for instance about three millimeters. Further, the diameter of the enlarged knob may be about two to about ten millimeters, for instance about four millimeters. In addition, particular examples of the elongated body include a height of about ten to about thirty millimeters, for instance about sixteen millimeters.

Figure 2:
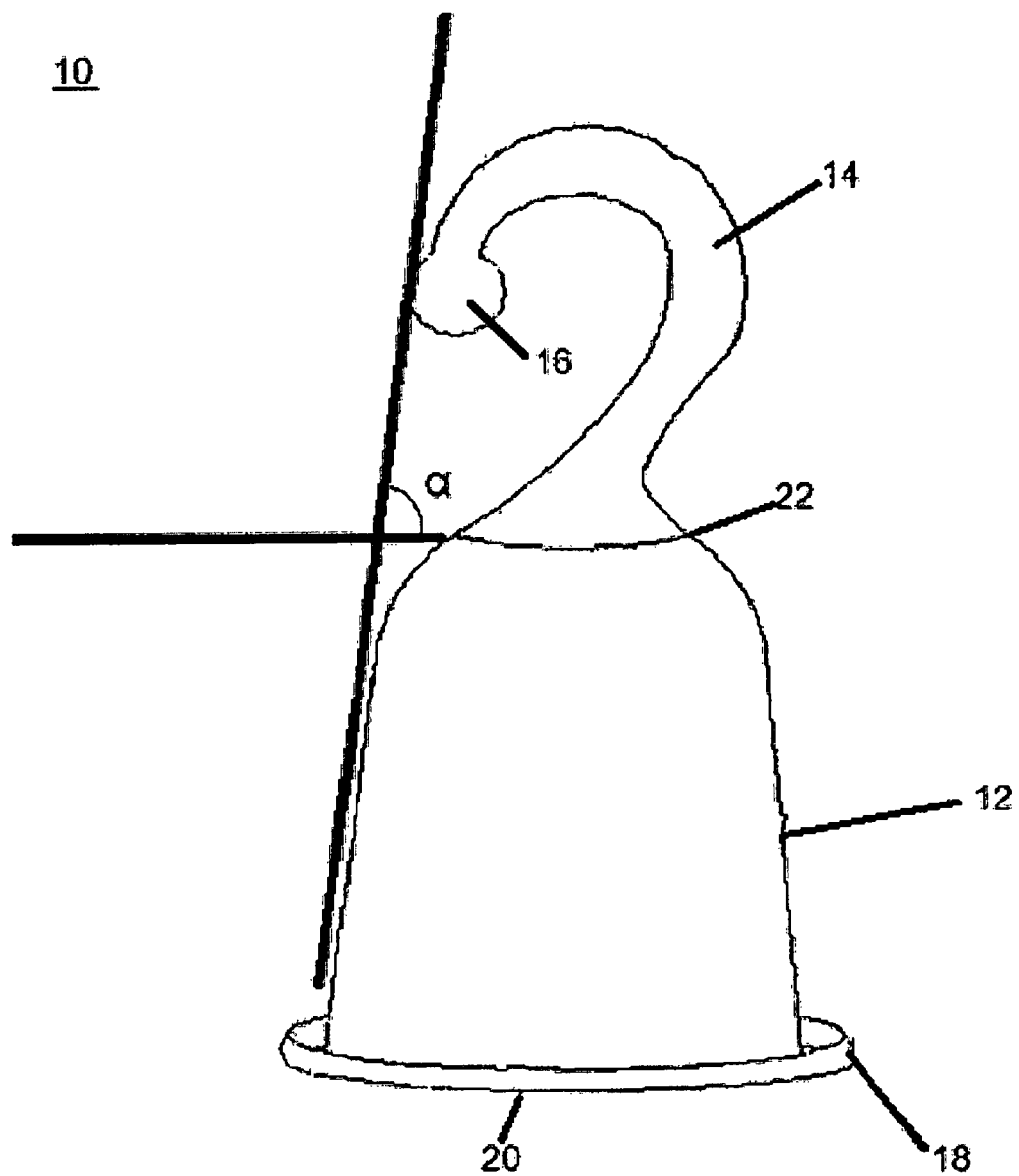
FIG. 2 is another front perspective view of the embodiment introduced in FIG. 1.

FIG. 2 introduces one example of the removal device 10 wherein the distal end of the hook, i.e. the enlarged knob, is generally aligned substantially parallel to an axis of the finger cot 12. The Applicants have discovered unexpected results for aligning the hook 14 on the wearer's finger, i.e. along the finger opening 20 axis, to the positioning of any of the rings and units as shown herein. Further, in particular examples, the outer face of the hook, i.e. the elongated knob 16, is offset at an angle alpha from the finger opening 20 axis.

Figure 3:
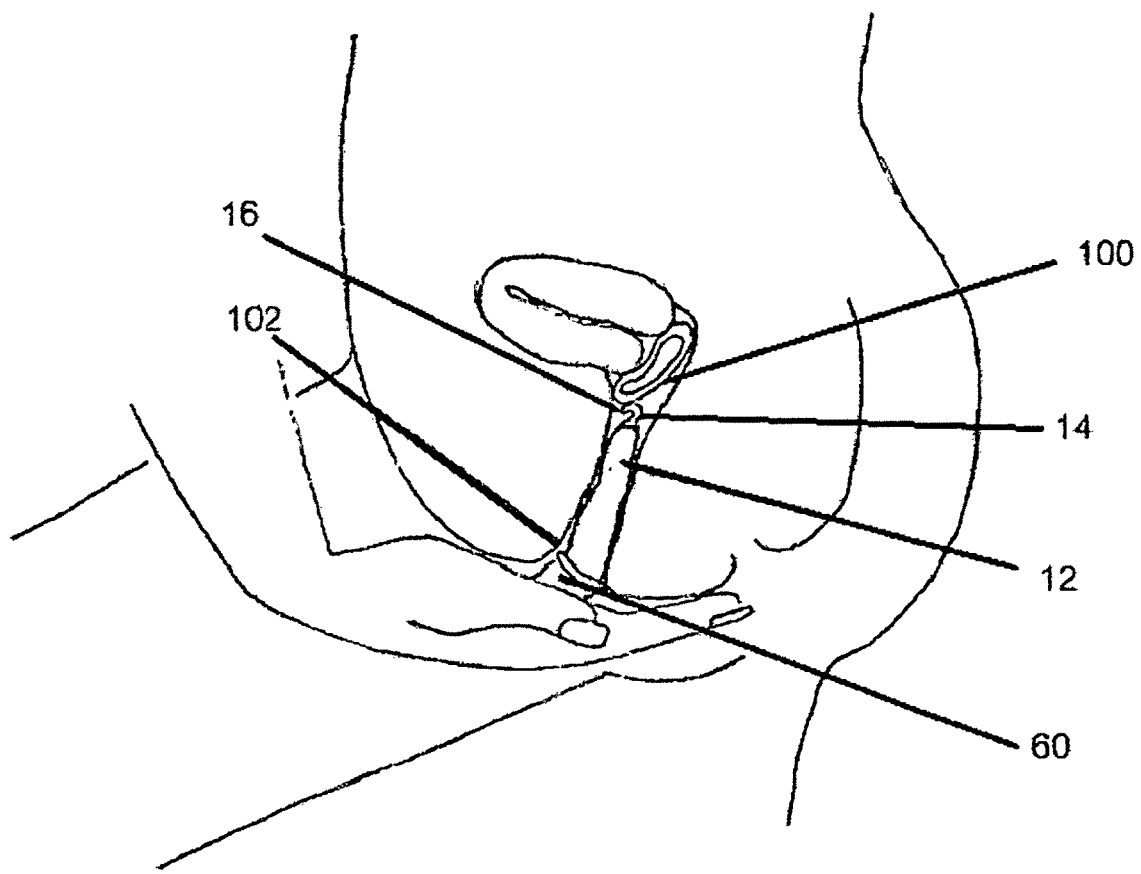
FIG. 3 is a schematic diagram of the embodiment of FIG. 1 in an operating position.

FIG. 3 shows one example of the removal device worn on the wearer's finger 60 and being inserted into the vaginal cavity 102 to remove a drug delivery ring 100. As shown, the finger cot 12 hygienically fully encloses the finger 60 when positioned in the vaginal cavity 102. The hook 14 is generally aligned substantially parallel to an axis of the finger cot 12 to improve alignment of the device directly to the drug delivery ring 100 when in the operating position. Therefore, the hook's 14 parallel alignment to the axis of the finger cot 12 reduces, or eliminates, the user's uncomfortable need to search for the ring or similar unit when positioned against the cervix. Similarly, the hook 14 is offset from the finger cot 12 to properly provide leverage when engaging the rim of the drug delivery ring 100 in the operating position. Other examples include a variety of finger cot 12 and hook 14 shapes, styles, and sizes for the convenience of its user.

Figure 4:
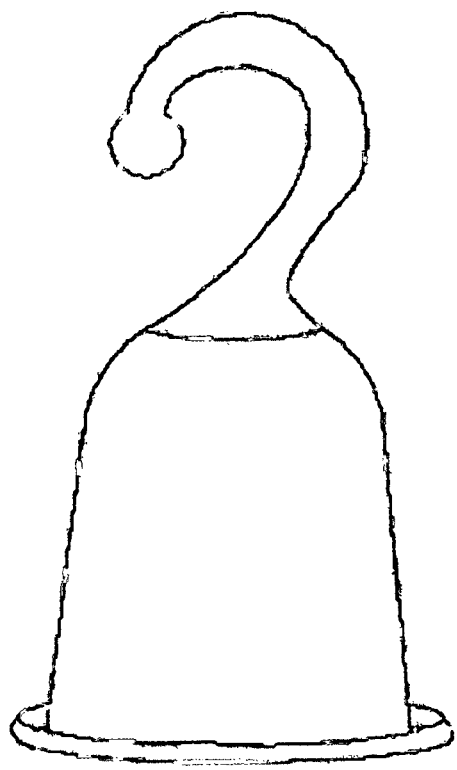
FIG. 4 is a side perspective view of the removal unit according to an embodiment of the disclosure.
Figure 5:
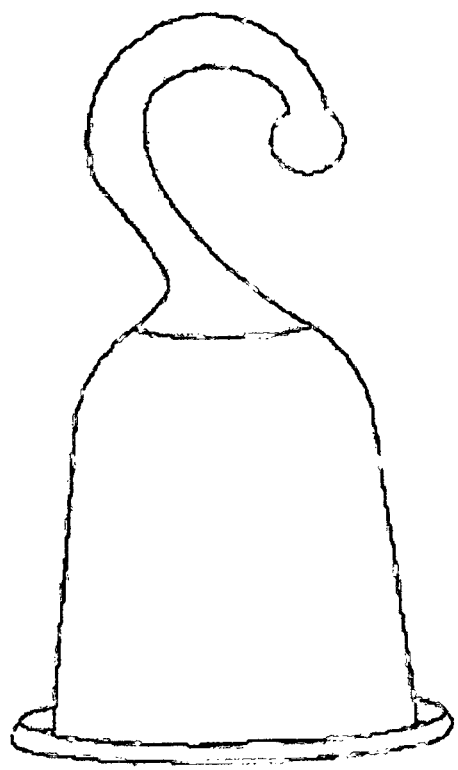
FIG. 5 is the opposing side perspective view of the removal unit according to an embodiment of the disclosure.
Figure 6:
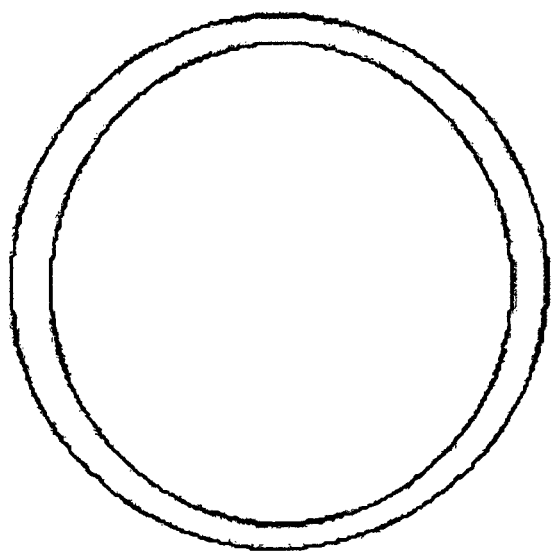
FIG. 6 is a bottom view of the removal unit.
Figure 7:
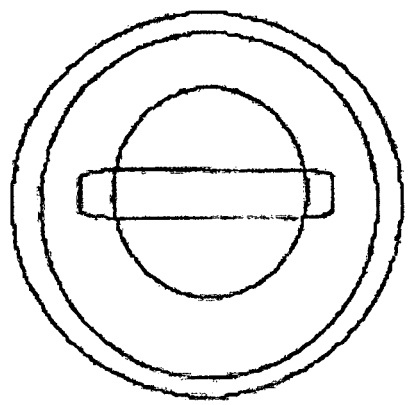
FIG. 7 is a top perspective view of the removal unit.

FIGS. 4-7 are the ornamental design for a removal device as shown and described. FIG. 4 shows a left perspective view of one embodiment of a removal device. FIG. 5 is a right perspective view of the embodiment of FIG. 4. FIG. 6 is a bottom view of the embodiment of FIG. 4. FIG. 7 is a top view of the embodiment of FIG. 4.

When worn in the operating position, i.e. when the finger cot 12 encloses the user's finger, the hook 14 is properly positioned to contact and engage a drug delivery ring at the cervix in the vaginal canal. The removal device 10 provides a tool for limited operation time in the vaginal canal to minimize excessive irritation to the vaginal walls, for instance due to repeated removal attempts and/or fingernail scraping, of a naked finger as presented in the conventional methods. The user is able to reach the vaginal ring with at least the tip of the finger through the advantages of the hook extensions shown and described herein. The user hooks the ring and removes the ring. Similarly, the hook may retrieve loose condoms and the like.

In other embodiments, the disclosure includes an intravaginal drug delivery ring kit. The kit may provide a removal device 10 and a drug delivery ring 100. The kit may comprise a removal device having a finger cot, e.g. any of the finger cot elements and examples previously shown or described. Further, the kit may comprise a hook, e.g. any of the hook elements and examples previously shown or described. In addition, the kit may comprise a drug delivery ring 100 as understood by those of ordinary skill in the art having the benefit of this disclosure.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. A device for removing an intravaginal drug delivery ring, the device comprising:
    an integral one-piece finger cot and a substantially rigid hook configured to remove said ring without injuring a vaginal cavity;
    wherein said finger cot includes a finger opening, a closed end, a compression band, and an expandable sleeve;
    wherein said hook extends away from said finger cot in a first direction and towards said finger cot in a second direction; and
    wherein a distal end of said hook is aligned substantially parallel to a central axis of said finger opening and at an angle offset from said central axis.

2. The device of claim 1, wherein said expandable sleeve comprises a moisture impermeable layer chosen from latex, polyurethane, polyisoprene, lambskin cellulose, and a combination thereof.

3. The device of claim 1, wherein said finger cot defines an elongated sleeve adapted to enclose a finger.

4. The device of claim 1, wherein a distal portion of said finger cot includes an upper tapered wall.

5. The device of claim 1, wherein said closed end of said finger cot is substantially parallel with said finger opening.

6. The device of claim 1, wherein said hook includes a wide proximate base adjacent to said closed end of said finger cot.

7. The device of claim 1, wherein said hook includes an elongated substantially one hundred and eighty degree curved body.

8. The device of claim 1, wherein said distal end of said hook includes an enlarged knob adapted to engage said ring.

9. The device of claim 8, wherein said ring is defined by a folded intravaginal drug delivery ring.

10. A device for removing an intravaginal contraceptive protection unit, the device comprising:
    an expandable finger cot adapted to enclose a finger, said finger cot comprising a finger opening, a closed end, an expandable sleeve and a compression band; and
    a substantially rigid hook configured to remove said intravaginal contraceptive protection unit without injuring a vaginal cavity, said hook extending from a top of said closed end, said hook having an elongated body and an engagement knob, wherein said engagement knob is positioned below at least a portion of said elongated body and is substantially parallel to an axis of said finger cot.

11. The device of claim 10, wherein said intravaginal contraceptive protection unit is chosen from a drug delivery unit, a male condom, a female condom, and a combination thereof.

12. The device of claim 10, wherein said hook extends away from said finger cot in a first direction and towards said finger cot in a second direction.

13. The device of claim 10, wherein said engagement knob is offset from said finger cot.

14. The device of claim 13, wherein said engagement knob is offset at an angle in the range of about ten degrees to about forty degrees from said finger cot.

15. The device of claim 10, wherein a distance between said engagement knob and said elongated body is about is about twice a height of said elongated body.

16. The device of claim 10, wherein said closed end of said finger cot is substantially parallel with said finger opening.

17. The device of claim 10, wherein said elongated body includes about a one hundred and eighty degree curve.

18. The device of claim 10, wherein said knob includes a nook adapted to engage a rim of a folded intravaginal drug delivery ring.

19. A device for removing an intravaginal drug delivery ring from a cervix with a single finger, the device comprising:
    an integral one-piece finger cot and a substantially rigid hook configured to remove said ring without injuring a vaginal cavity;
    wherein said finger cot includes a finger opening, a closed end, a compression band and an expandable sleeve adapted to enclose a finger;
    wherein said hook includes an elongated body extending substantially one hundred and eighty degrees from said finger cot and a distal end of said hook includes an enlarged knob aligned substantially parallel to a central axis of said finger opening and at an angle offset from said central axis; and
    wherein said enlarged knob includes a diameter greater than a diameter of the elongated body and is spaced about eight millimeters from said elongated body, said knob being configured to engage a folded intravaginal drug delivery ring at said cervix.

* * * * *